United States Patent [19]
Taepke

[11] Patent Number: 6,152,885
[45] Date of Patent: Nov. 28, 2000

[54] BAROMETRIC PRESSURE SENSOR FOR USE WITH IMPLANTABLE ABSOLUTE PRESSURE SENSOR

[75] Inventor: Robert T. Taepke, Coon Rapids, Minn.

[73] Assignee: Medtronic, Inc., Minneapolis, Minn.

[21] Appl. No.: 09/070,366

[22] Filed: Apr. 30, 1998

[51] Int. Cl.[7] ..................................................... A61B 5/00
[52] U.S. Cl. .............................................................. 600/561
[58] Field of Search ................................... 600/585, 486, 600/561, 587

[56] References Cited

U.S. PATENT DOCUMENTS

| | | | |
|---|---|---|---|
| 4,407,296 | 10/1983 | Anderson | 128/675 |
| 4,791,931 | 12/1988 | Slate | 128/419 |
| 5,330,505 | 7/1994 | Bloom | 607/6 |
| 5,346,518 | 9/1994 | Baseman | 55/267 |
| 5,368,040 | 11/1994 | Carney | 128/700 |
| 5,535,752 | 7/1996 | Halperin et al. | 128/670 |
| 5,564,434 | 10/1996 | Halperin et al. | 128/748 |
| 5,692,637 | 12/1997 | Hodge . | |
| 5,810,735 | 9/1998 | Halperin | 600/486 |

FOREIGN PATENT DOCUMENTS

| | | | |
|---|---|---|---|
| 8707850 | 6/1987 | WIPO | D15/701 |

*Primary Examiner*—Cary O'Connor
*Assistant Examiner*—Pamela Wingood
*Attorney, Agent, or Firm*—Michael B. Atlass; Harold R. Patton

[57] ABSTRACT

A barometric pressure sensor for deriving reference pressure data for use in combination with absolute pressure data derived by an implantable medical device (IMD) is disclosed. The barometric pressure sensor is located in a sensing module adapted to be located with the patient's body having a module housing enclosing an air chamber which encloses the barometric pressure sensor. An air vent extends through the module housing for venting the air chamber to atmospheric pressure outside the module housing. A protective vent cover extends across the air vent formed of a material capable of air passage and capable of inhibiting passage of moisture, liquids, and particulate contaminants through the air vent and into the air chamber. In one embodiment, the sensing module is adapted to be worn or carried by the patient and includes operating circuitry and a power supply for powering the barometric pressure sensor and periodically storing sensed atmospheric pressure values as reference pressure data. In another embodiment, the sensing module comprises a percutaneous access device which is adapted to be implanted in the skin and subcutaneous tissue layer of the patient and includes the protective vent cover extending across the air vent formed in the percutaneous access device. The percutaneous access device is coupled with the barometric pressure sensor to provide for an air chamber extending between the protective vent cover and the barometric pressure sensor. The barometric pressure sensor is preferably enclosed within an air chamber of the implantable medical device, and a catheter extends between the air chamber of the implantable medical device and the percutaneous access device.

4 Claims, 7 Drawing Sheets

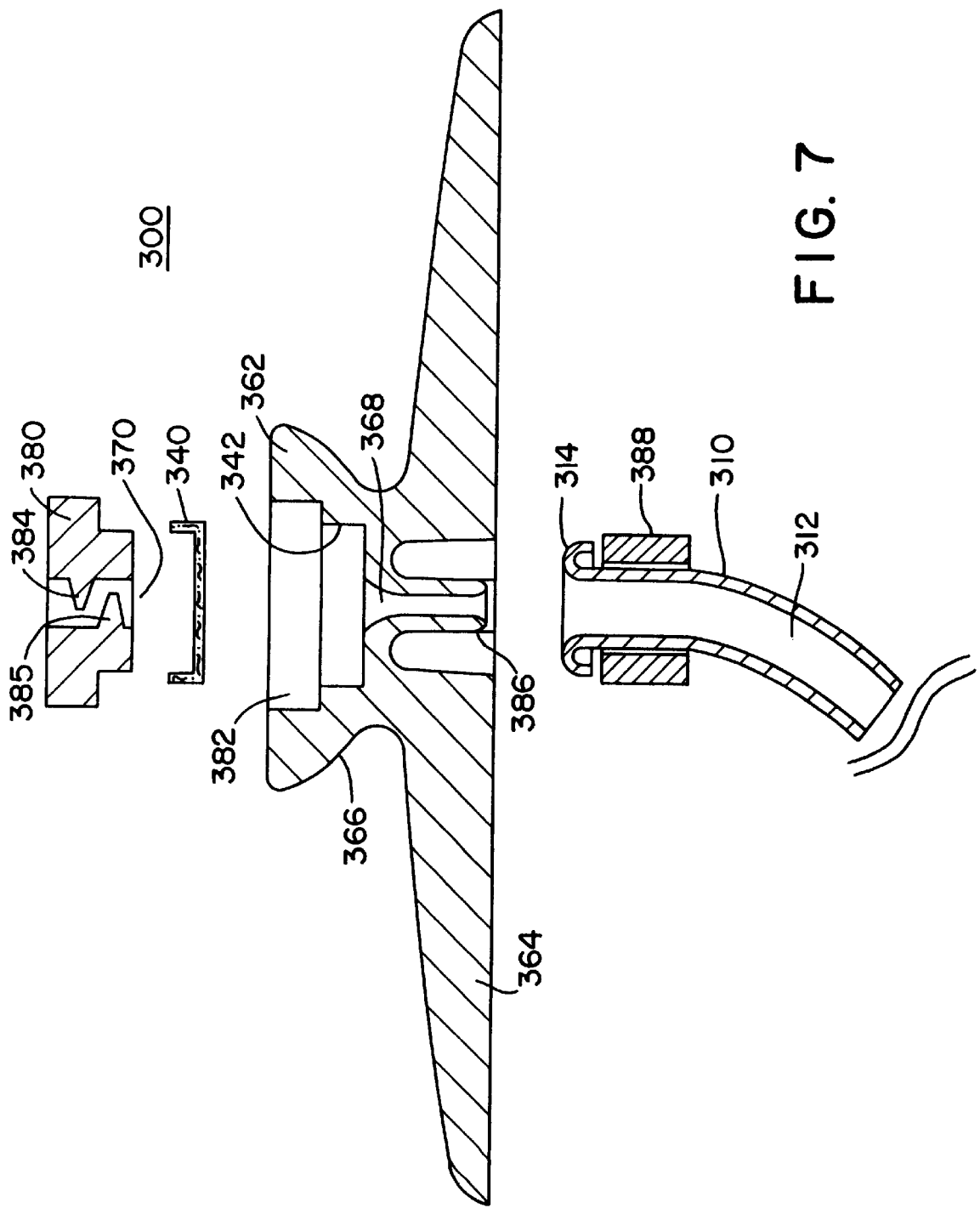

BAROMETRIC PRESSURE SENSOR FOR USE WITH IMPLANTABLE ABSOLUTE PRESSURE SENSOR

CROSS-REFERENCE TO RELATED APPLICATION

Reference is hereby made to commonly assigned, co-pending U.S. patent application Ser. No. 09/070,310 filed Apr. 30, 1998 for IMPLANTABLE MEDICAL DEVICE FOR SENSING ABSOLUTE BLOOD PRESSURE AND BAROMETRIC PRESSURE by Miesel et al.

FIELD OF THE INVENTION

The present invention relates to a barometric pressure sensor for deriving reference atmospheric pressure data for use in combination with absolute pressure data derived by an implantable medical device (IMD) and particularly to the fabrication of various embodiments of the barometric pressure sensor to inhibit passage of liquid and particulate contaminants through an air vent to the air chamber containing the barometric pressure sensor.

BACKGROUND OF THE INVENTION

A great many IMDs for cardiac monitoring and/or therapy comprising sensors located in a blood vessel or heart chamber coupled with an implantable monitor or therapy delivery device have been proposed or implemented. For example, such cardiac IMDs include implantable heart monitors and therapy delivery devices including pacemakers, cardioverter/defibrillators, cardiomyostimulators, ischemia treatment devices, and cardiac drug delivery devices. All of these systems include electrodes for sensing and sense amplifiers for recording and/or deriving sensed event signals from the intracardiac electrogram (EGM). In current implantable cardiac devices providing a therapy the sensed event signals are utilized to control the delivery of the therapy in accordance with an operating algorithm and at least selected EGM signal segments and sensed event histogram data or the like are stored in internal RAM for telemetry out to an external programmer in real time or at a later time.

Efforts have also been underway for many years to develop implantable physiologic signal transducers and sensors for temporary or chronic use in a body organ or vessel usable with such IMDs for monitoring a physiologic condition other than or in addition to the EGM to derive and store data and/or to control a therapy delivered by the IMD. A comprehensive listing of implantable therapy delivery devices are disclosed in conjunction with implantable sensors for sensing a wide variety of cardiac physiologic signals in U.S. Pat. No. 5,330,505, incorporated herein by reference.

Blood pressure signal values respond to changes in cardiac output that may be caused by a cardiac failure, e.g., fibrillation or high rate tachycardia, or that may reflect a change in the body's need for oxygenated blood. In the former case, monitoring of a substantial drop in blood pressure in a heart chamber, particularly the right ventricle, alone or in conjunction with an accelerated or chaotic EGM, was proposed more than thirty years ago as an indicia of fibrillation or tachycardia that could be used to trigger automatic delivery of defibrillation or cardioversion shock. More recently, it has been proposed to monitor the rate of change in blood pressure (dP/dt) that accompany normal heart contraction and relaxation and blood pressure changes that occur during high rate tachycardia and fibrillation or flutter.

A number of cardiac pacing systems and algorithms for processing the monitored mean blood pressure or monitored dP/dt have been proposed and, in some instances employed clinically, for treating bradycardia. Such systems and algorithms are designed to sense and respond to mean or dP/dt changes in blood pressure to change the cardiac pacing rate in a rate range between an upper and a lower pacing rate limit in order to control cardiac output. adjoining blood vessels and heart chambers during the cardiac cycle, blood temperature, blood pH, and a variety of blood gases. Such Implantable hemodynamic monitors and blood pressure and temperature sensors that derive absolute blood pressure signals and temperature signals are disclosed in commonly assigned U.S. Pat. Nos. 5,368,040, 5,535,752 and 5,564,434, and in U.S. Pat. No. 4,791,931, all incorporated by reference herein. The MEDTRONIC® Chronicle™ Implantable Hemodynamic Monitor (IHM) employs the leads and circuitry disclosed in the above-incorporated, commonly assigned, '752 and '434 patents to record the EGM and absolute blood pressure values for certain intervals. The recorded data is periodically transmitted to a programmer operated by the physician in an uplink telemetry transmission from the IHM during a telemetry session initiated by a downlink telemetry transmission from the programmer's radio frequency (RF) head and receipt of an interrogation command by the IHM.

Certain of the measured physiologic signals derived from the heart or blood in the circulatory system are affected by ambient conditions that cannot be separately measured by the above-described IMDs and physiologic sensors. Specifically, blood pressure signal values derived by a wholly implantable system, e.g., the IHM described above are affected by atmospheric pressure acting on the patient. Blood temperature signal values derived by a wholly implantable system, e.g., that disclosed in the above-referenced '752 and '434 patents, are affected by ambient temperature or by a fever afflicting the patient, respectively.

Changes in ambient conditions other than weather changes can also influence the measurement of absolute blood pressure changes, including both mean or average blood pressure and dP/dt, by implantable pressure sensors. For example, when a patient in which such an implantable blood pressure sensing medical device is implanted changes elevation by ascending or descending in an elevator in a tall building or in an airplane, the change in barometric pressure mask changes that are sought to be measured. In the context of an implantable rate responsive pacemaker operating under a rate control algorithm, the pressure change caused by the elevation change itself may exceed the blood pressure change that reflects a change in exercise level of the patient and be misinterpreted as meriting a change in pacing rate to the upper or lower pacing rate limit, which can, at least, be uncomfortable to the patient. The barometric pressure effect can similarly have a negative effect on operating and detection functions of other IMDs reliant on accurately sensing cardiac blood pressure changes that truly reflect a cardiac function or requirement for cardiac output.

The deleterious effect of barometric pressure on cardiac blood pressure measurement has been noted. In commonly assigned U.S. Pat. No. 4,407,296, a micro-machined pressure sensor is disposed at the distal end of a lead in an oil filled chamber on one side of a pressure sensor element that is closed by a flexible membrane. The membrane is disposed behind a protective grill at the distal tip of the lead within which blood fluids can contact the exposed side of the membrane. Blood pressure changes deflect the membrane, and the deflection is transmitted through the oil to the micro-machined pressure sensor element which is deflected to produce a pressure signal value change proportional to the blood pressure change acting on the membrane. The blood pressure change reflects both the blood pumping action of the heart and the ambient atmospheric pressure acting on the patient's body. In a first embodiment, the effect of atmospheric pressure is attempted to be offset by providing a chamber behind the sensor element that is sealed at a known average atmospheric pressure. In practice, this approach has proven to be inadequate because the known pressure cannot account for changes in barometric pressure and renders the blood pressure measurements ambiguous.

In a second embodiment, the chamber behind the sensor element is filled with oil and extends proximally through a lumen of the lead body to a further positioned in the subcutaneous cavity under the patient's skin where the implantable monitor or pulse generator is implanted. In this case, the membrane on the lead body is difficult to manufacture, fragile and can become obstructed in chronic implantation. Moreover, the oil filled lumen can be generally either vertical or horizontal in all or in part depending on a number of factors, including the implantation path of the lead body between the subcutaneous cavity and the implantation site of the pressure sensor in the patient's heart chamber and whether the patient is upright or supine. The force that the oil in the oil filled lumen applies to the pressure sensor element depends on the orientation of the lumen with respect to the force of gravity which can change as the patient changes posture. Therefore, the force of the oil column biases the pressure sensor element in an unpredictable manner, and the reference pressure varies unpredictably and may not represent barometric pressure.

In recognition of these problems with absolute pressure sensors employed to measure blood pressure in a heart chamber or blood vessel, it is suggested in the above-incorporated, commonly assigned, '752 and '434 patents that the patient be provided with a belt worn, external pressure recorder that records and time stamps recordings of barometric pressure that can be retrieved and used for comparison with the internally recorded absolute blood pressure data. Such an external barometric pressure recorder is intended to be used with the above-referenced MEDTRONIC® Chronicle™ IHM. The barometric pressure reference values that are periodically stored in the memory of the external recorder are read out at the time that the absolute pressure data is telemetered out. The reference values are subtracted from the absolute values to derive the relative pressure values.

The barometric pressure sensor is contained in an air chamber within the housing of the external pressure recorder. The air pressure in the air chamber is expected to equalize with atmospheric pressure by air passage through seams that remain when the housing halves are assembled together. Moisture, liquids, can accumulate in the air chamber. For example, the patient might get caught in a rainstorm or splash water on or drop the pressure sensor module into water, allowing water to contact the barometric pressure sensor, and dust can enter the seams and accumulate on the barometric pressure sensor. These contaminants can alter the barometric pressure sensor response to atmospheric air pressure, resulting in the storage of corrupted barometric pressure values which are not possible to detect. The corrupted reference pressure values can therefore contribute to erroneous relative cardiac pressure values when the stored reference pressure values are subtracted from the telemetered out absolute pressure values.

Despite the considerable effort that has been expended in designing such IMDs and associated sensors for sensing such physiologic signals, a need exists for a system and method for accurately accounting for ambient conditions surrounding the patient that affect the sensed and measured physiologic signal values, particularly in the case of blood pressure.

SUMMARY OF THE INVENTION

It is therefore an object of the present invention to provide a more tightly sealed barometric pressure sensing module adapted to be associated with a patient and usable in the context of recording barometric pressure signal values as reference pressure data with an air vent for venting the air chamber enclosing the barometric pressure sensor while inhibiting the ingress of moisture, water, and particulate contaminants into the air chamber.

In accordance with the present invention, a barometric pressure sensor for deriving reference pressure data for use in combination with absolute pressure data derived by an IMD is located in a sensing module adapted to be located with the patient's body having a module housing enclosing an air chamber which encloses the barometric pressure sensor. An air vent extends through the module housing. A protective vent cover extends across the air vent formed of a material capable of air passage and capable of inhibiting passage of moisture and particulate contaminants through the air vent and into the air chamber.

In one embodiment, the sensing module is adapted to be worn or carried by the patient and includes operating circuitry and a power supply for powering the barometric pressure sensor and periodically storing sensed atmospheric pressure values as reference pressure data. In another embodiment, the sensing module comprises a "stoma" implant or percutaneous access device which is adapted to be implanted in the skin and subcutaneous tissue layer of the patient and includes the protective vent cover extending across the air vent formed in the percutaneous access device. The percutaneous access device is coupled with the barometric pressure sensor to provide for an air chamber extending between the protective vent cover and the barometric pressure sensor. The barometric pressure sensor is preferably enclosed within an air chamber of the implantable medical device, and a catheter extends between the air chamber of the implantable medical device and the percutaneous access device.

The present invention advantageously avoids passage of moisture and particulate contaminants through the air vent and the accumulation thereof in the air chamber. The storage of corrupted barometric pressure values which are not possible to detect is prevented.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein:

recording absolute blood pressure values and a externally worn, barometric pressure sensor module for recording reference pressure values in which the present invention can be implemented;

FIG. 7 is an enlarged exploded cross-section view of the percutaneous access device of FIGS. 5 and 6 illustrating the manner in which the air vent is covered by a moisture inhibiting protective vent cover to maintain the catheter air lumen open and uncontaminated with fluid or other contaminants.

DETAILED DESCRIPTION OF THE PREFERRED EMBODIMENTS OF THE INVENTION

Figure 1:
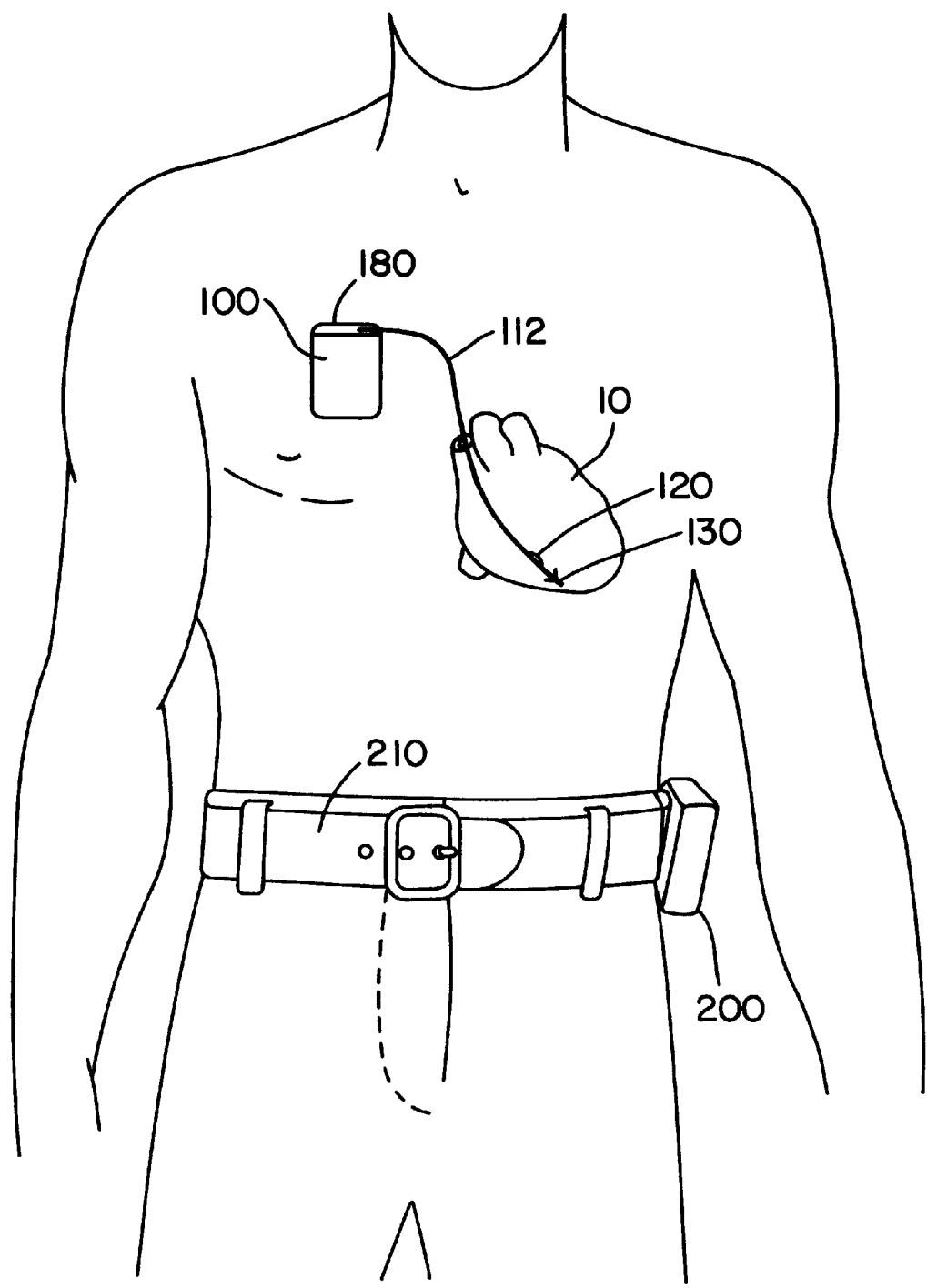
FIG. 1 shows a diagram illustrating a Prior Art system including an implantable medical device coupled to an absolute cardiac blood pressure sensor.

FIG. 1 is a schematic illustration of a prior system including an IMD 100 coupled to an absolute cardiac blood pressure sensor 120 in a patient's heart 10 for recording absolute blood pressure values and a externally worn, barometric pressure sensor module 200 for recording reference pressure values in which the present invention can be implemented. The IMD 100 is depicted implanted subcutaneously in the patient's chest region, and it is coupled at its connector module 180 to a lead 112 extending through blood vessels into the right ventricle of the patient's heart 10. The barometric pressure sensor module 200 is worn by the patient on the belt 210 or on a pendant or the like.

The blood pressure sensor 120 is located on lead 112 just proximal to a lead distal tip fixation mechanism 130 for fixing it in position despite continuous movement of the heart 10. In the preferred embodiments, the lead 112 and blood pressure sensor 120 correspond to those disclosed in detail in the above-incorporated, commonly assigned, '434 and '752 patents for deriving absolute blood pressure and temperature signals, but other blood pressure sensors could be employed.

Such an IMD 100 that provides a therapy and/or monitors a physiologic condition or state is programmable and/or can be interrogated by an external programmer through the use of bi-directional RF telemetry that exchanges data and commands via uplink and downlink RF telemetry transmissions through the patient's skin. In the context of an implantable blood pressure monitor, a series of absolute blood pressure signal values are sensed periodically or in response to a signal provided by a patient operated controller, e.g., a permanent magnet applied over the IMD 100 to close a magnetic field sensitive reed switch or the like. The series of absolute blood pressure value signals are stored as blood physician can associate the episode recorded with a time of day and any other recollection of the patient.

The absolute blood pressure data is stored on a FIFO basis in memory within the IMD 100 for telemetry out to an external programmer in an uplink RF telemetry transmission initiated by a medical care provider or physician. The physician uses the external programmer to generate and transmit an interrogation command via a downlink telemetry transmission to the IMD 100 which recognizes the command and initiates the uplink telemetry transmission of the stored absolute pressure data in response. The stored absolute pressure data is received and stored in a file in memory of a personal computer based programmer and reviewed or processed as described below.

As described above, the sensed cardiac blood pressure values are influenced by barometric pressure acting on the patient's body. The absolute blood pressure sensor 120 can only sense the absolute blood pressure levels which include the blood pressure fluctuations that accompany cardiac contraction and relaxation and the underlying barometric pressure. Consequently, the absolute blood pressure signal values that are sensed, stored in memory in IMD 100, and subsequently transmitted to the external programmer must be corrected for barometric pressure. In order to do so, it is necessary to record the barometric pressure value affecting the patient at or close to the time that the absolute blood pressure values are sensed and stored in the barometric pressure sensor module 200. The barometric pressure sensor module 200 periodically samples the barometric pressure and records the barometric pressure values with time stamps in memory in the barometric pressure sensor module 200. An RS-232 port is provided for bi-directional communication through a cable with a personal computer based programmer. The physician can make the connection and transfer or copy the contents of the memory in the barometric pressure sensor module 200 into a file in the personal computer memory and ultimately onto is then corrected using the stored barometric pressure data to derive relative blood pressure data that reflects blood pressure of the heart.

In the prior art barometric pressure sensor module, the barometric pressure sensor is located in an interior air chamber, and atmospheric air vents through seams in the module housing so that the air chamber housing the barometric pressure sensor is at atmospheric pressure. The seams also admit moisture and particulate contaminants and can leak liquids, e.g., water, through the seams if the exterior housing gets wet.

Figure 2:
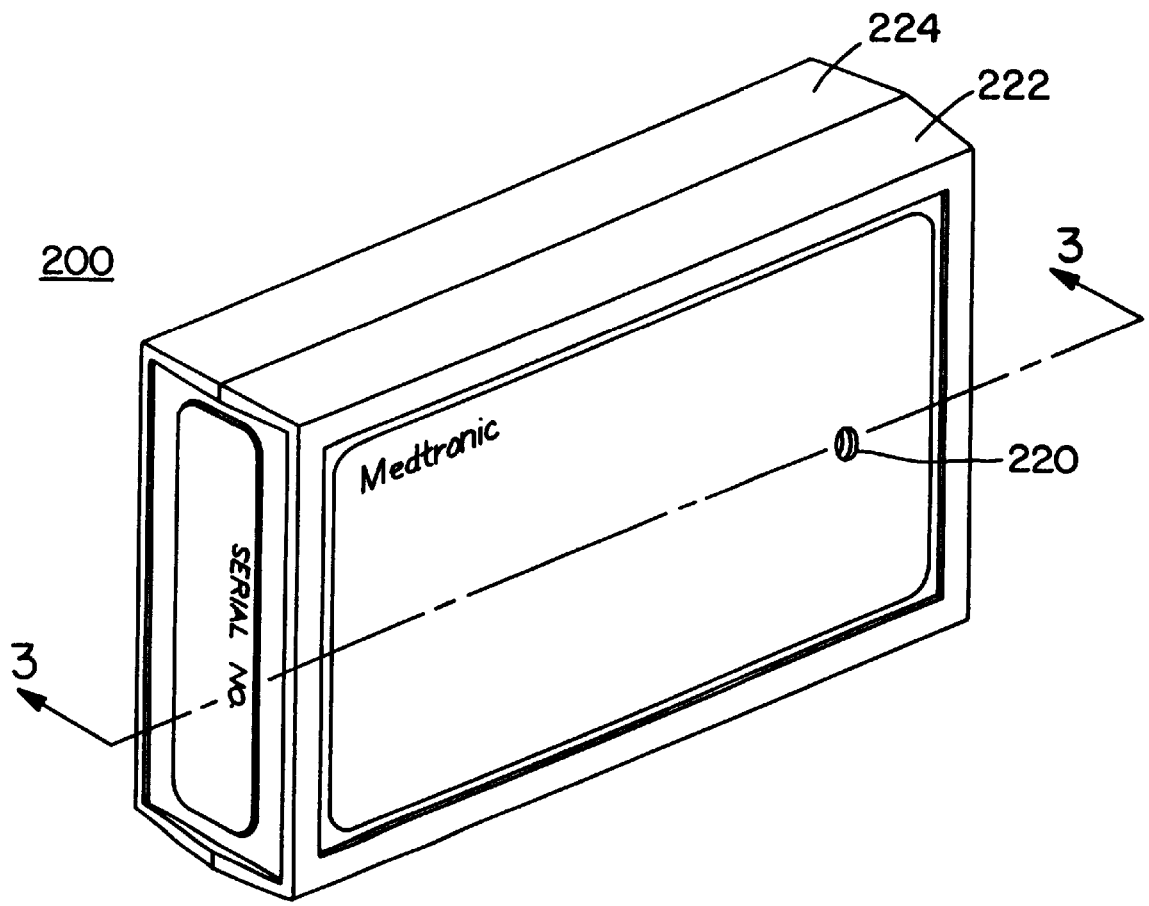
FIG. 2 is a perspective view of the barometric pressure sensor module of the type depicted in FIG. 1 having an dedicated air vent in the module housing extending between the atmosphere and the air chamber of the module housing containing a reference barometric pressure sensor.
Figure 3:
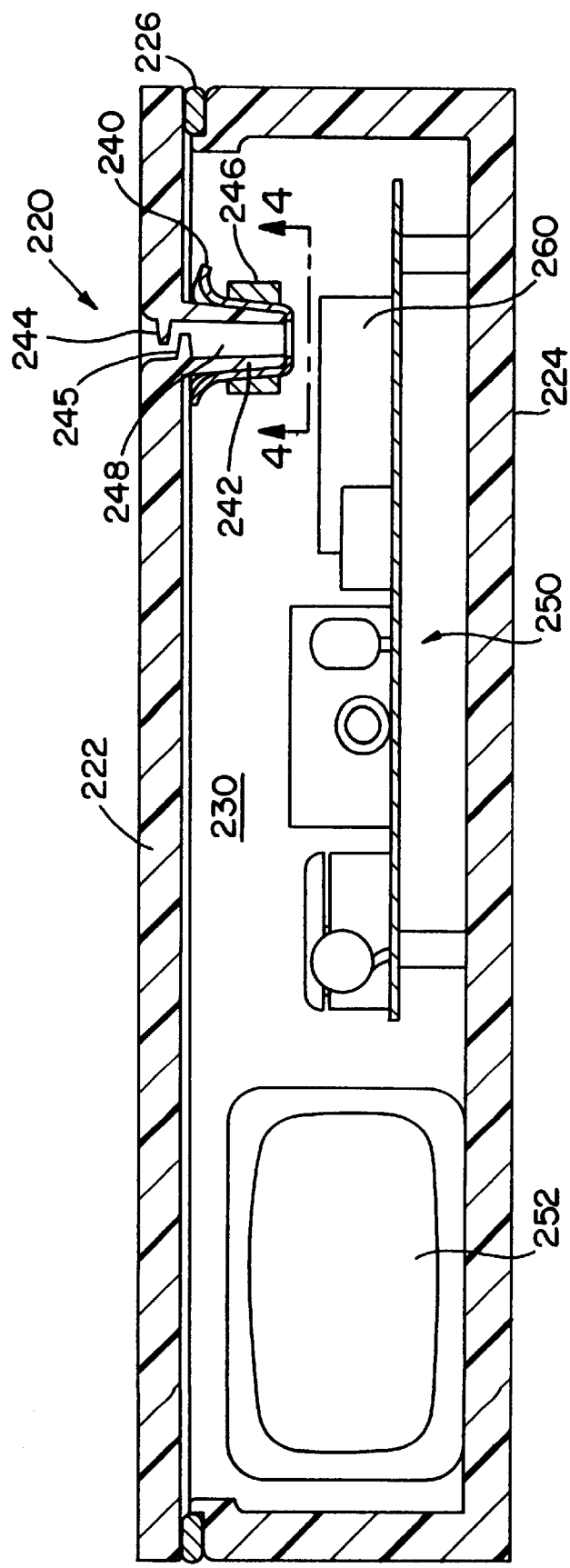
FIG. 3 is a cross-section view taken along lines 3—3 in FIG. 2 depicting the air vent through the pressure sensor module housing and a protective vent cover for inhibiting ingress of moisture and contaminants into the air chamber of the module housing.

FIG. 2 is a perspective view of the barometric pressure sensor module 200 of the present invention showing the dedicated air vent 220 extending through the module housing cover 222 which is sealed to a module housing 224. The dedicated air vent 220 extends between the atmosphere and an interior air chamber containing the barometric pressure sensor and electronic circuitry. FIG. 3 is a cross-section view showing the dedicated air vent 220 into the air chamber 230 and the electronic circuitry 250, battery 252, and barometric pressure sensor 260 housed in the air chamber 230. The electronic circuitry 250 includes circuits for timing the periodic sensing of the air pressure within the air chamber 230 and storing the sensed barometric pressure signal value as a reference pressure value in RAM and circuits for enabling transmission of the stored reference pressure values to a personal computer based programmer. The air chamber 230 of the barometric pressure sensor module housing 224 is sealed by attachment of the module housing cover 222 against the resilient seal 226 overlying the rim of the module housing 224.

The dedicated air vent 220 includes an air porous, protective vent cover 240 for inhibiting ingress of moisture, liquids, and contaminants into the air chamber 230 of the module housing 224. The air vent 220 is formed by a tubular projection 242 of the housing cover 222 into the air chamber defining an elongated air passage 248 extending through it. Laterally projecting baffles 244 manner. The laterally projecting baffles 244 and 245 block inadvertent puncture of the air porous, protective vent cover 240 with any sharp object, e.g., a needle or electrical connector pin or the like, erroneously inserted into the air passage 248.

Figure 4:
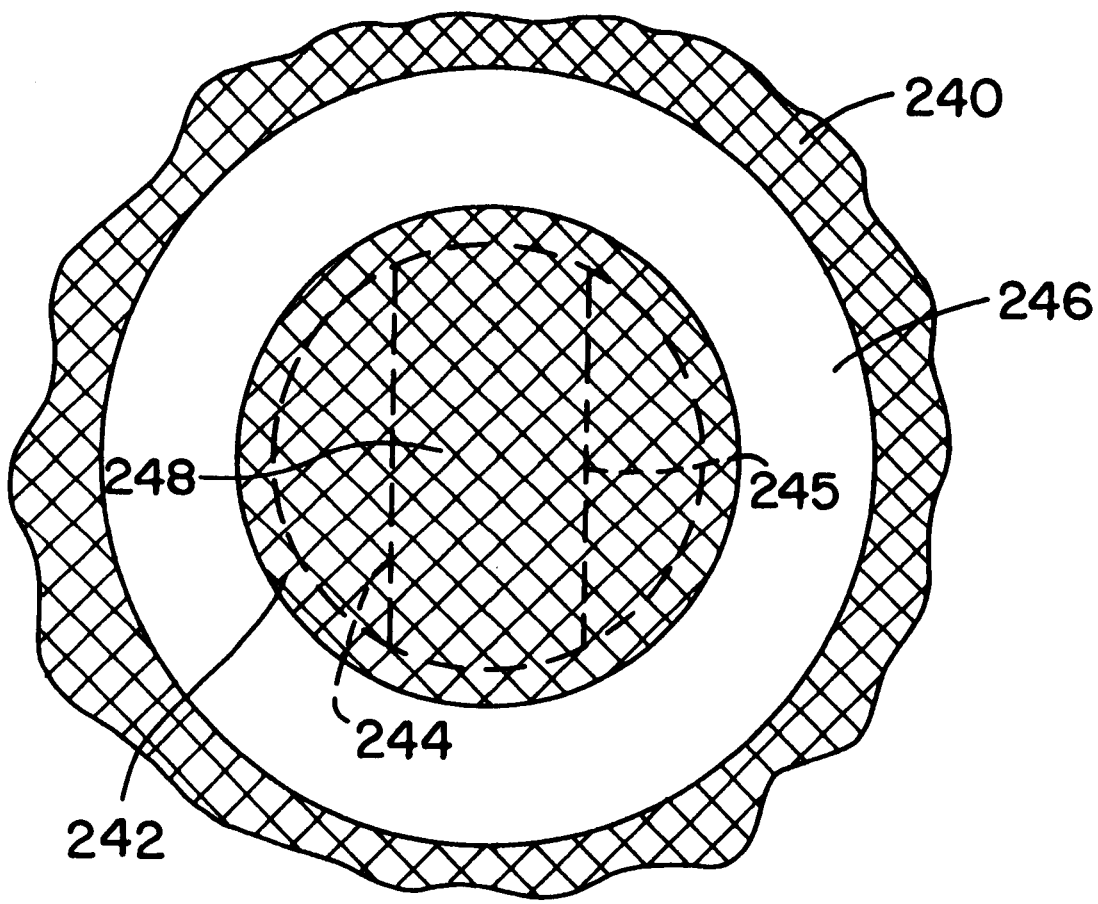
FIG. 4 is an end view of the manner in which the air vent is covered by the protective vent cover to protect the barometric pressure sensor and circuitry within the pressure sensor module housing air chamber from contamination.

FIG. 4 is an end view from inside air chamber 230 of the manner in which the air vent 220 is covered by the protective vent cover 240 to protect the barometric pressure sensor 260 and circuitry 250 of FIG. 3 from contamination by passage of moisture, liquids, and particulate contaminants that enter air passage 248 into the air chamber 230 of FIG. 3. FIG. 4 also shows the overlapping baffles 244 and 245 extending across the air passage 248 in broken lines. The protective vent cover 240 is formed of a tightly woven synthetic fabric, e.g. Gore-Tex® fabric, that passes air, including water vapor, but blocks passage of any liquids and moisture, e.g., dew, or particulate contaminants through it and into the air chamber 230 of FIG. 3. The protective vent cover 240 is cut into a circular pattern and fitted over the projecting end of the tubular projection 242 to extend across the end of the elongated air passage 248. The retention ring 246 is press fit over the fabric and presses it against the side wall of the tubular projection 242 to hold it in place. An adhesive can also be applied to retain these components in place.

Figure 5:
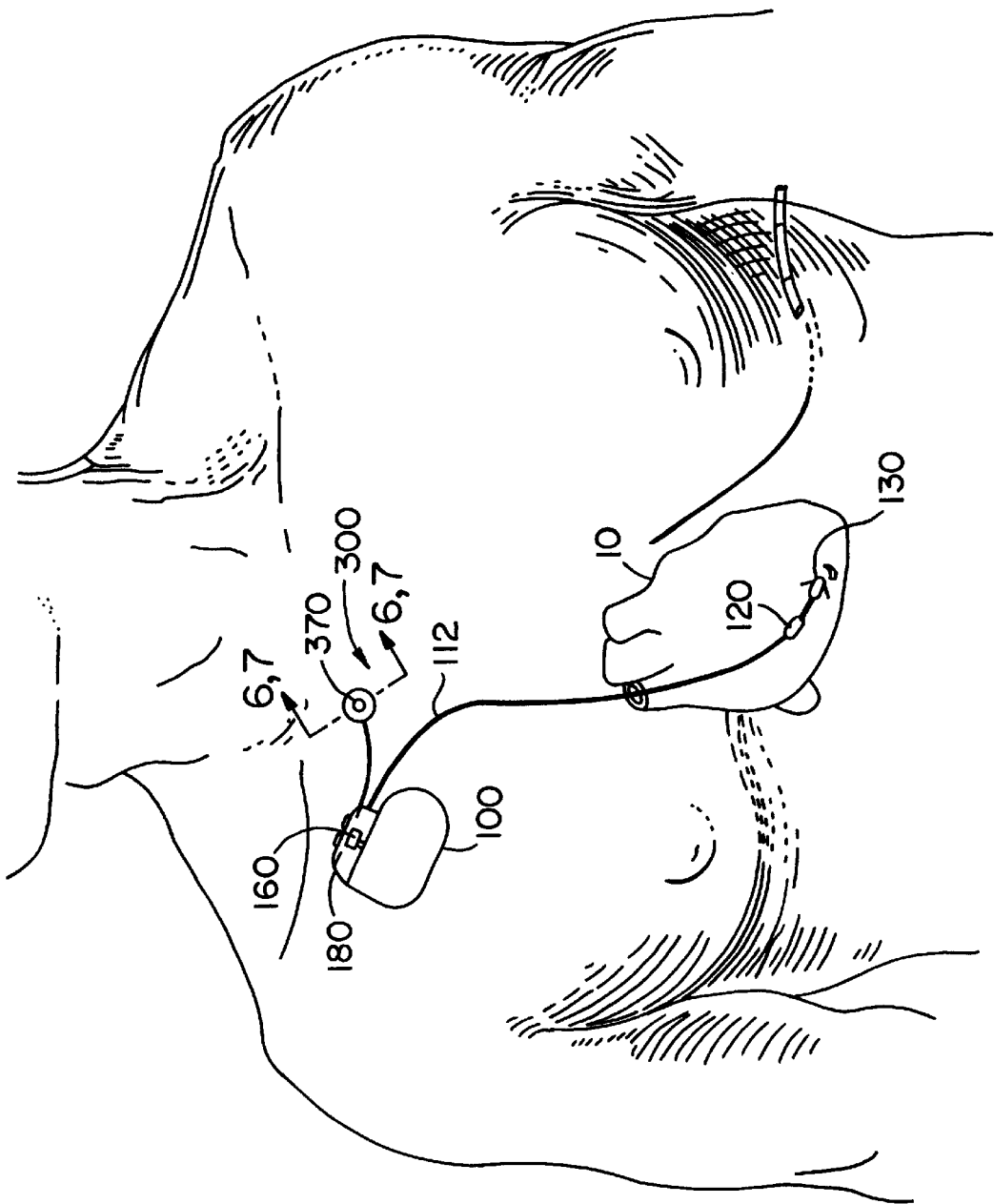
FIG. 5 is a schematic illustration of an IMD coupled to an absolute cardiac blood pressure sensor in a patient's heart for recording absolute blood pressure values and coupled to a percutaneous access device extending through the patient's skin and exposed to atmospheric pressure.

FIG. 5 is a schematic illustration of an IMD 100 coupled to an absolute cardiac blood pressure sensor 120 in a patient's heart 10 for sensing absolute blood pressure values and coupled to a stoma implant or percutaneous access device 300 extending through the patient's skin and exposed to atmospheric pressure. The percutaneous access device 300 provides for an air vent 370 extending through the patient's skin and to a barometric pressure sensor 160 in or on the connector module 180 of the IMD 100. As noted below, the barometric pressure sensor can be alternatively located in the percutaneous access device 300 with a lead extending to the connector module 180 in a manner disclosed in atmosphere, a reference pressure can be sensed and stored or otherwise employed in the IMD 100 to derive and store relative blood pressure values.

Figure 6:
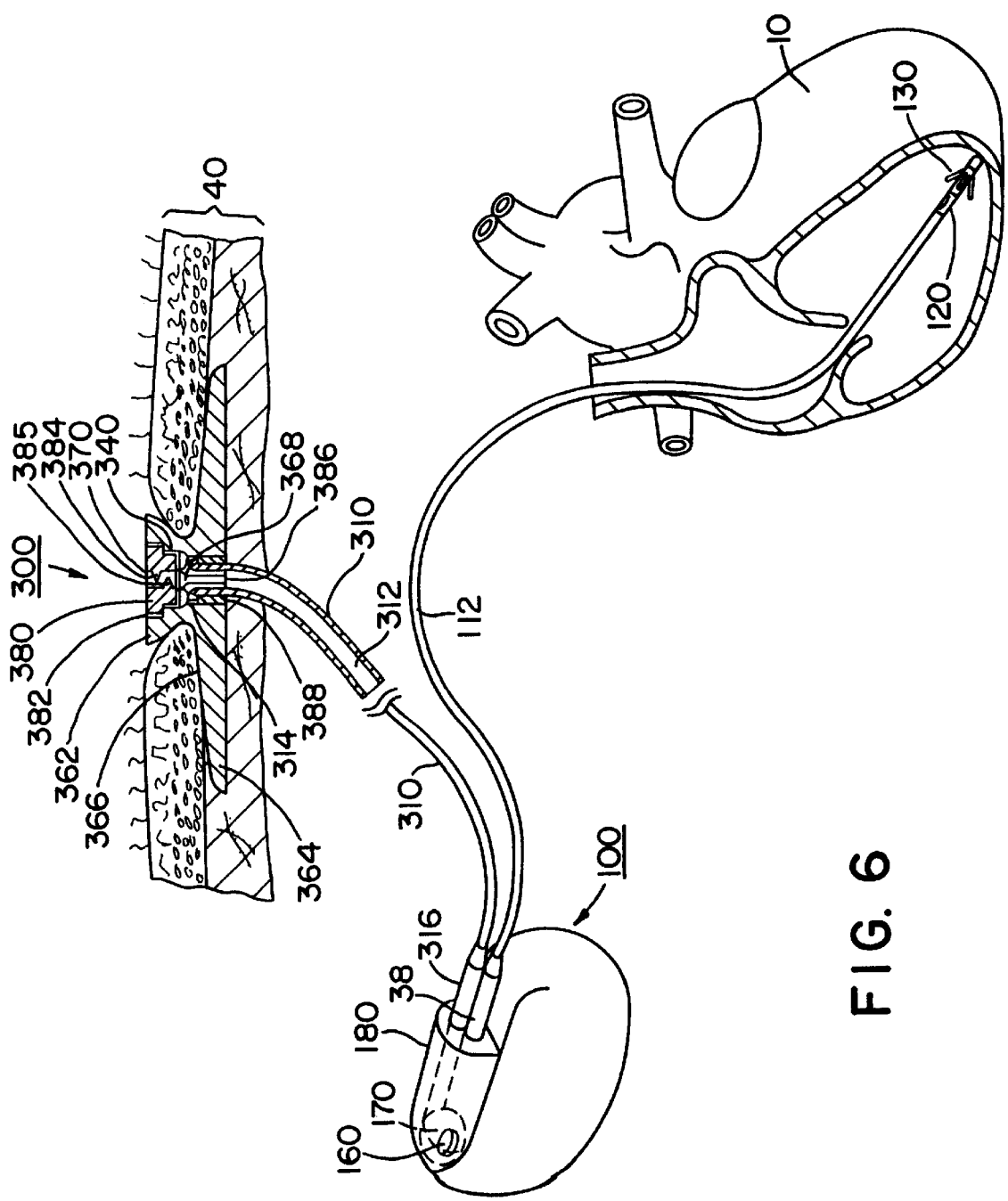
FIG. 6 is a schematic, partial cross-section, illustration of an IMD coupled to an absolute cardiac blood pressure sensor in the patient's heart for recording absolute blood pressure values and having a barometric pressure sensor in or on the connector module of the IMD coupled by a catheter air lumen to an air vent in the percutaneous access device covered by a protective vent cover for sensing reference pressure values therethrough.

FIG. 6 is a schematic, partial cross-section, illustration of the construction and implantation of the percutaneous access device 300 which is coupled to the connector module 180 by a catheter 310 to allow the IMD 100 to sense barometric pressure to provide a reference pressure value. The connector module 180 is coupled to an absolute cardiac blood pressure sensor 120 in the patient's heart 10 to allow sensing of the absolute blood pressure values provided to the IMD 100 for processing with the reference pressure values. FIG. 7 is an enlarged exploded cross-section view of the percutaneous access device 300 of FIGS. 5 and 6 illustrating the manner in which the air vent 370 is covered by a protective vent cover 340 (of the same type as protective vent cover 240 described above with reference to FIGS. 3 and 4) to maintain catheter lumen 312 open and uncontaminated with moisture, liquids or other particulate contaminants.

FIGS. 6 and 7 schematically illustrate these variations of such a system employing a percutaneous access device 300 that is chronically implanted in the patient's skin and subcutaneous tissue layer. Such percutaneous access devices are well known in the prior art and are employed as vascular access devices for periodic catheterization of blood vessels, as electrode terminals or as drug delivery access ports or other devices for obtaining chronic access within the body or to allow body fluids or waste to be expelled. Such percutaneous access devices and are formed of a bio-compatible material, e.g., pyrolytic carbon, that is surface treated in a variety of ways to encourage tissue growth around the exterior surface thereof so that it is not expelled from the skin.

The percutaneous access device 300 is formed like a bobbin, having a plate-like exterior flange 362 and a plate-like interior flange 364 coupled together by a cylindrical side wall 366 and is chronically implanted in the patient's skin and subcutaneous tissue layer. The upper and lower flanges 362 and 364 are also skin and subcutaneous tissue layer 440. When the components of the percutaneous access device 300 are assembled together, an elongated air passage 368 is aligned with an air vent 370, and an air porous, waterproof fabric, protective vent cover 340 extends across the junction of air passage 368 and air vent 370. Again, the protective vent cover 340 is formed of Gore-Tex® fabric or the like that allows air and vapor to permeate therethrough while inhibiting the passage of moisture, liquids and particulate contaminants therethrough. The air passage 368 can be viewed as an air chamber or part of an air chamber which is at atmospheric air pressure because of air permeation via the protective vent cover 340.

In this embodiment, the barometric pressure sensor 160 is mounted on or in the connector module 180 such that its pressure sensing diaphragm or transducer is disposed in an air chamber 170 enclosed within the connector module 180 that is open to one of the connector bores and then coupled with the air passage 368 through the lumen 312 of catheter 310. The barometric pressure sensor may correspond to the pressure and temperature sensor disclosed in detail in the above-incorporated, commonly assigned, '434 and '752 patents, but other blood pressure sensors could be employed. It will be understood that FIG. 6 is intended to illustrate the interconnection of the percutaneous access device 300 with any manner of mounting the barometric pressure sensor on or in the connector module 180 or the housing of the IMD 100. The barometric pressure sensor 160 is located within an air chamber 170 that is impervious to fluid penetration and that extends to the air passage 368 when a connection is made with a catheter 310 as described below.

In this embodiment and in reference to FIGS. 6 and 7, the air vent 370 is formed in a cylindrical stopper 380 that fills a cylindrical bore 382 in the upper flange 362. The air vent 370 in the cylindrical stopper 380 includes laterally extending baffles 384 and 385 to prevent the inadvertent puncture with any sharp cover 340 is placed in a seat 342 between the planar interior surfaces of the cylindrical stopper 380 and the cylindrical bore 382, and the cylindrical stopper 380 is sealed into the cylindrical bore 382 In this way, the protective vent cover 340 is retained, and moisture and contaminants are prevented from entering the air passage 368. However, air pressure within the air passage 368 is at the barometric pressure outside the patient's skin and tissue layer 40.

A catheter 310 is provided that encloses a catheter lumen 312 extending between a proximal catheter connector end 316 and a distal catheter end 314. The distal catheter end 314 is coupled to the air passage 368 of the percutaneous access device 300. This coupling is effected by flaring and fitting the distal catheter end 314 over a tube 386 extending downwardly in a cylindrical bore 388 so that the catheter lumen 312 is aligned with a tube lumen forming the air passage 368. A press fit ferrule 388 fills the space within the cylindrical bore receiving the distal catheter end 314 surrounding the tube 386 to mechanically hold the distal catheter end 314 against the side wall of the tube 386. The press fit ferrule therefore maintains the distal catheter end 314 in position and seals air passage 368 and catheter lumen 312 from ingress of liquids or contaminants.

The air passage 368 is empty and vented to atmosphere through the air vent 370 and protective vent cover 340. In this manner, an air column extends from the air passage 368 through the catheter lumen 312 and to an air chamber 170 enclosing the barometric pressure sensor 160 preferably mounted on or in the connector module 180. In the embodiment illustrated in FIG. 6, the proximal catheter connector end 316 is fitted into a bore into the connector module 180, which bore extends to the air chamber 170, and is sealed there to prevent the ingress of body fluids into the air column provided by catheter lumen 314. It will be understood that the proximal catheter connector end 316 could also surround a barometric pressure sensor projecting outward of the connector module 180 or could otherwise mate with the barometric pressure sensor than depicted in FIG. 6. manufacture so that the catheter 310 is permanently attached at its proximal end to the connector module 180 and at its distal end to the percutaneous access device 300.

In a further variation of this depicted embodiment, the barometric pressure sensor can be mounted onto the percutaneous access device 300 so that the pressure sensitive diaphragm or transducer is aligned with air passage 368. In such a case, a lead body extends between the barometric pressure sensor and a connector bore of the connector module 180 to make an electrical connection with the IMD 100. Such a variation is disclosed in the above-referenced (P-2711) application.

The preceding specific embodiments are therefore to be understood as illustrative of the many ways in which the principles of the invention may be practiced. It is to be understood, therefore, that other expedients known to those of skill in the art or disclosed herein may be employed without departing from the invention or the scope of the appended claims. It is therefore to be understood, that within the scope of the appended claims, the invention may be practiced otherwise than as specifically described without actually departing from the spirit and scope of the present invention.

What is claimed is:

1. A system for measuring barometric pressure for use in generating reference pressure values in conjunction with measurement of absolute pressure values within a patient's body comprising:

a barometric pressure sensing module adapted to be located with the patient's body having a module housing enclosing an air chamber, wherein the module housing is adapted to be implanted in the patient's skin and subcutaneous tissue layer;

a percutaneous access device coupled to the barometric pressure sensing module to expose the air chamber to the atmosphere outside the patient's body;

a barometric pressure sensor within the air chamber for generating reference pressure values representing the ambient air pressure in the air chamber; and a protective vent cover extending over the air vent formed of a material capable of air passage and capable of inhibiting passage of moisture, liquids, and particulate contaminants through the air vent and into the air chamber.

2. A system for measuring barometric pressure for use in generating reference pressure values in conjunction with measurement of absolute pressure values within a patient's body comprising:

a barometric pressure sensing module adapted to be located with the patient's body having a module housing enclosing an air chamber;

a barometric pressure sensor within the air chamber for generating reference pressure values representing the ambient air pressure in the air chamber;

an air vent extending through the module housing for venting the air chamber to atmospheric pressure outside the module housing; and a protective vent cover extending over the air vent formed of a material capable of air passage and capable of inhibiting passage of moisture, liquids and particulate contaminants through the air vent and into the air chamber, wherein the air vent is tubular in cross-section and at least one baffle is located within the air vent between an exterior air vent opening and the protective vent cover to block entrance of objects capable of penetrating the protective vent cover.

3. The system of claim 2, wherein the protective vent cover is formed of a fabric material that allows passage of air and water vapor.

4. The system of claim 1, wherein the protective vent cover is formed of a fabric material that allows passage of air and water vapor.

* * * * *